United States Patent [19]

Brunsting et al.

[11] 4,341,993
[45] Jul. 27, 1982

[54] REFLECTOR OPTICS WITH IMPEDANCE SENSING ORIFICE

[75] Inventors: Albert Brunsting, Miramar; Walter R. Hogg; William A. Newton, both of Dade County, all of Fla.

[73] Assignee: Coulter Electronics, Inc., Hialeah, Fla.

[21] Appl. No.: 181,447

[22] Filed: Aug. 25, 1980

[51] Int. Cl.³ .................................. G01N 27/00
[52] U.S. Cl. .................... 324/71 CP; 250/458.1
[58] Field of Search ......... 250/458; 324/71 R, 71 PC; 235/92 PC

[56] References Cited

U.S. PATENT DOCUMENTS 3,910,702 10/1975 Corll .......................... 324/71 CP
3,941,479 3/1976 Whitehead ................. 324/71 CP

*Primary Examiner*—Michael J. Tokar
*Attorney, Agent, or Firm*—Gerald R. Hibnick

[57] ABSTRACT

A particle analyzing apparatus comprising a reflector chamber containing an electrolyte and having a concave reflector surface with a first focus and a second focus; entraining structure, having an introduction tube for providing and moving a stream of particles suspended in an electrolyte solution through the first focus; a source of radiant energy for illuminating the particles as they pass through the first focus to produce a source of detectable radiation signals, which reflect off the concave reflector surface to be subsequently collected and analyzed; an exit tube coaxially aligned with the introduction tube; a sensing orifice mounted in the tip of the introduction tube or the exit tube; and a pair of energized electrodes disposed in the electrolyte solution on either side of the orifice, whereby the orifice creates a constricted electrical path in which the stream of particles generate electrical impedance signals as they move therethrough.

16 Claims, 4 Drawing Figures

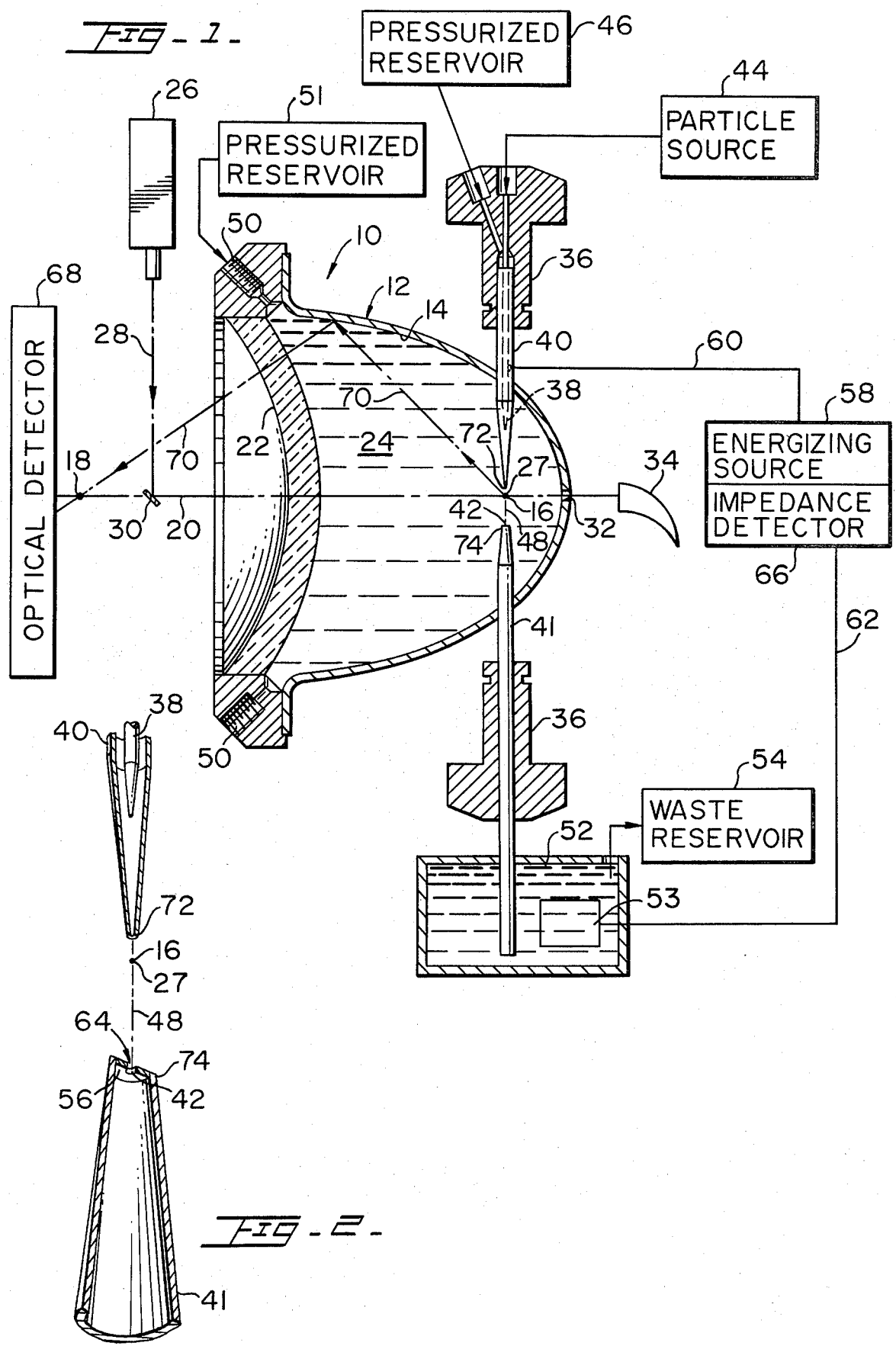

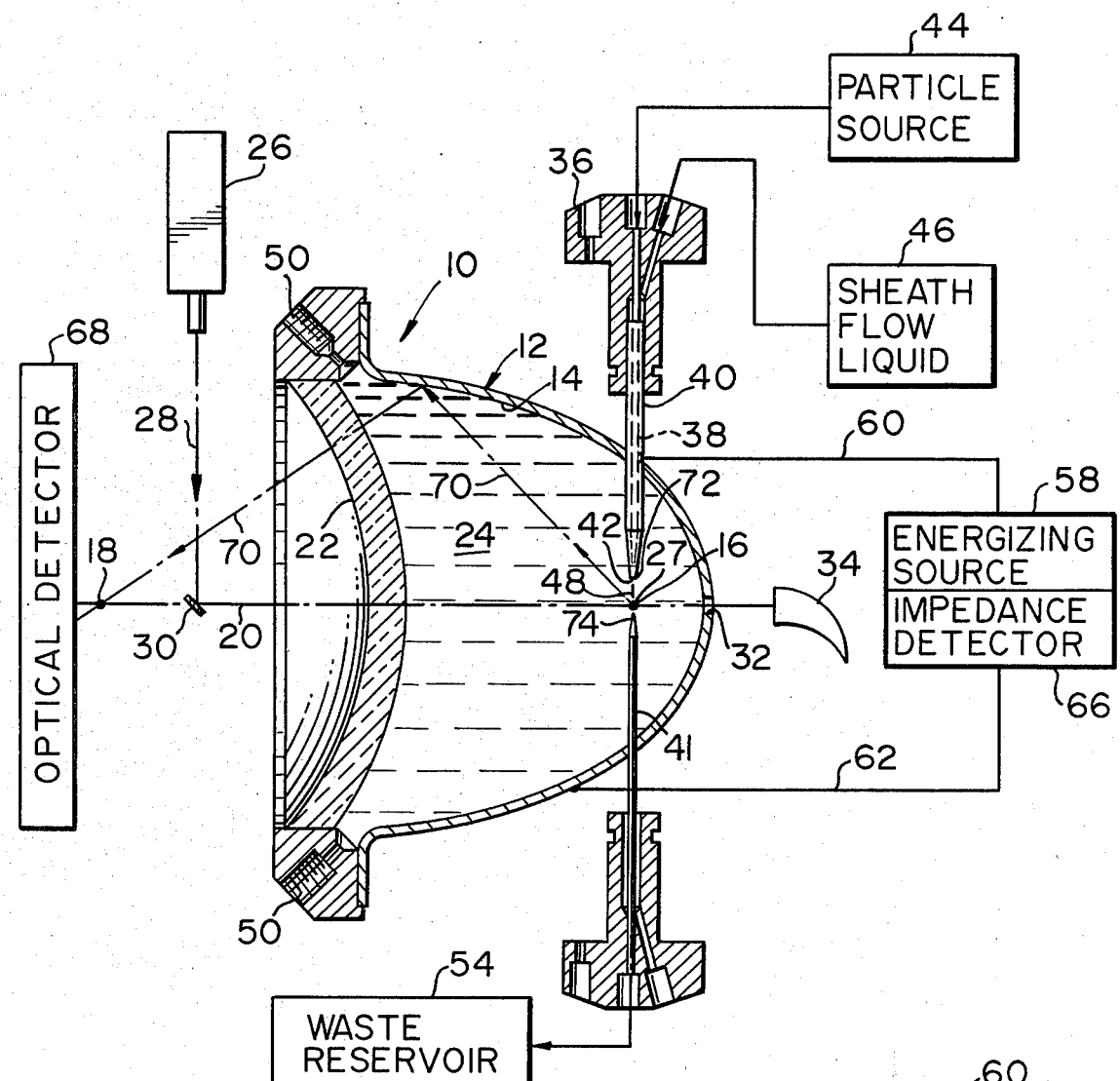
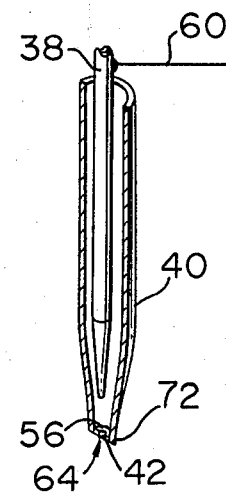

REFLECTOR OPTICS WITH IMPEDANCE SENSING ORIFICE

BACKGROUND OF THE INVENTION

1. Field of the Invention

The invention relates to particle analyzers wherein electronic impedance measurements and optical measurements are made on particles entrained in a liquid stream.

2. Description of the Prior Art

Since its conception more than 25 years ago, the principle of particle counting and sizing invented by Wallace H. Coulter has resulted in numerous methods and apparatuses for the electronic counting, sizing, and analysis of microscopic particles, which are scanned in a fluid suspension, as shown by the pioneer U.S. Pat. No. 2,656,508 to Coulter. In this prior art arrangement, a D.C. electric current flow is established between two vessels by suspending electrodes in the respective bodies of the suspension fluid. The only fluid connection between the two bodies is through an orifice; hence, an electric current flow and field are established in the orifice. The orifice and the resultant electric field in and around it constitute a sensing zone. As each particle passes through the sensing zone, for the duration of the passage, the impedance of the contents of the sensing zone will change, thereby modulating the electric current flow and electric field in the sensing zone, and hence causing the generation of a signal to be applied to a detector suitably arranged to respond to such change. (The mark "Coulter" is a registered trademark, Registration No. 995,825, of Coulter Electronics, Inc. of Hialeah, Fla.) The heretofore described particle analyzers will be referred to as "impedance sensing particle analyzers".

Numerous particle analyzers have been developed wherein optical measurements, such as scattered light detection, fluorescent light detection, and light absorbance detection, are made on an entrained stream of particles. These particle analyzers will be hereinafter referred to as "optical particle analyzers". The most advanced state of the art for optical particle analyzers is shown in U.S. Pat. Nos. 4,188,542, 4,188,543, 4,189,236 and 4,199,686, the assignee therein being the same as in the present invention. Each of these patents are incorporated by reference herein. Each of these optical particle analyzers is directed toward using reflector optics for collecting large solid angle optical signals emanating from a sensing zone whereat illuminating radiation impinges upon the stream of particles. The use of these wide angle collectors has resulted in greater light collection efficiency, better optical and hence electronic signal to noise ratios and the minimizing of the effects of preferential signal emissions in unpredictable directions. The improved sensitivity in detecting characteristics of biological cells, resulting from the utilization of these wide angle collectors, has opened new areas of cell analysis that heretofore were not available.

As can be seen from the prior art, the development of optical particle analyzers and impedance sensing particle analyzers have proceeded along different paths, without the two types of particle measurements being combined in a single apparatus. An impedance sensing orifice has been used in combination with downstream light absorbance detection, scattered light detection and fluorescent light detection, as disclosed in U.S. Pat. No. 3,710,933 to Fulwyler et al. U.S. Pat. No. 3,710,933 is incorporated by reference herein. However, the types of optical measurements made downstream from the orifice do not provide the type and quality of information, nor the sensitivity of detection, required for the hereinafter described invention.

In the Fulwyler particle analyzer of U.S. Pat. No. 3,710,933 and in the prior art apparatuses modeled thereafter, a pair of concentric tubes have been used, one tube for introducing the sample of suspended particles and the other tube for providing a first liquid sheath around the sample. The liquid sheath hydrodynamically focuses the particles as they pass through an orifice disc, which is mounted at the end of the sheath tube and has an impedance sensing orifice formed therein. By virtue of this arrangement, a second liquid sheath is required for hydrodynamically focusing the particles as they proceed from the orifice, through the optical sensing zone, into an exit tube or nozzle. This has been the accepted and only known way of accomplishing hydrodynamically focused movement of the particles through both an impedance sensing zone and a subsequent optical sensing zone for most of the last decade.

In addition to the optical disadvantages previously discussed, the above described Fulwyler particle analyzer has several other disadvantages. First, as shown by the design of the Fulwyler analyzer, it has always been assumed in accepted prior art practices, that the sensing orifice must be positioned upstream of the optical sensing zone. The sheath tube and orifice disc containing the sensing orifice must be made sufficiently large to provide structural strength. On the other hand, the particles must be very accurately aligned and hydrodynamically focused to pass through the relatively small optical sensing zone. Typically, a laser beam has a cross-sectional Gaussian intensity profile, and the particles must each pass through the center of the profile to be substantially uniformly irradiated at maximum intensities. Hence, the closer the end of the sheath tube is positioned to the optical sensing zone, the better the alignment of the particles through the optical sensing zone and therefore the better the optical signal resolution. Unfortunately, as will be seen in the hereinafter described invention, if light is to be collected in a nearly 4 solid angle, the large end of the sheath tube blocks a substantial portion of the light, if it is positioned in close proximity to the optical sensing zone, as is the case with the Fulwyler analyzer. Therefore, this prior art analyzer design creates a dilemna of having an undesirable tradeoff between having to sacrifice optical signal resolution or light collection efficiency or having to settle upon a less than satisfactory combination to minimize the two design problems.

SUMMARY OF THE INVENTION

The invention is directed toward a particle analyzing apparatus using a reflector chamber, containing a liquid and having at least a concave reflector surface. The reflector surface has a first focus defining an optical detection volume or sensing zone and is used for obtaining a large solid angle collection of detectable radiation signals, produced by irradiating a stream of electrolyte-suspended particles passing through the first focus. Two electrolyte containing vessels are provided, one of them comprising the reflector chamber, and are separated by an orifice arranged to receive the stream of particles. A pair of energized electrodes are positioned, one on each side of the orifice in the electrolyte solution, so that the orifice creates a constricted electrical path and the stream of particles generates electrical impedance signals. Consequently, the particle analyzing apparatus accomplishes both impedance measurements and optical measurements using at least one reflector for wide angle light collection, with all of its previously described advantages.

The reflector chamber is provided with at least one entrance tube, for introducing the particles, and an exit tube, for removing the particles, coaxially aligned to pass the particles through the first focus. An orifice disc, which has the orifice formed therein, is positioned in the end of the entrance or the exit tube. In one desirable implementation, the first focus is positioned in close proximity to the tube not having the orifice and is remotely disposed to the tube having the orifice. By virtue of this arrangement, the total solid angle subtended by the two tubes, with respect to the first focus, is substantially minimized, so that the collection of the detectable radiation signals is substantially maximized. This is highly desirable in that the tube having the orifice must have relatively large cross-sectional dimensions to provide structural strength for mounting the orifice disc.

In one particularly desirable embodiment, the orifice disc is positioned in the outward extremity of the exit tube. A liquid sheath is provided inside the entrance tube for hydrodynamically focusing the particle suspension. The first focus is positioned in close proximity to the entrance tube. Heretofore, it had been assumed in the prior art that the orifice disc and therefore the impedance sensing zone must be positioned upstream with respect to the optical sensing zone. Contrary to this prior art practice, the preferred embodiment is designed so that the orifice is downstream of the optical sensing zone. By virtue of this arrangement, the analyzer is relatively insensitive to coaxial misalignment of the entrance and exit tubes. Additionally, the continuous inner surface of the entrance tube allows for the development of highly non-turbulant, laminar liquid sheath therein for hydrodynamically focusing the particles for the optical sensing zone. In the prior art arrangement, the liquid flow in the entrance tube can be disrupted by the presence of the flow-traversing orifice disc. Additionally, the remote positioning of the sensing orifice greatly minimizes the solid angle subtended by the exit tube, with respect to the first focus, and thereby minimizes the loss in collecting detectable radiation signals.

DESCRIPTION OF THE DRAWINGS

Further objects and advantages of the present invention will become apparent as the following description proceeds, taken in conjunction with the accompanying drawings in which:

FIG. 1 shows a cross-sectional side view of a preferred embodiment of the particle analyzer of the invention; and FIG. 2 shows an enlarged fragmentary view of the ends of the tubes shown in FIG. 1.

FIG. 3 shows a cross-sectional side view of an alternative embodiment of the particle analzyer.

FIG. 4 shows an enlarged fragmentary view of the end of the entraining means shown in FIG. 3.

DETAILED DESCRIPTION OF THE PREFERRED EMBODIMENT

Disclosed is a particle analyzing apparatus for obtaining from an entrained stream of particles, such as biological cells, both optical measurements using reflector optics and electronic impedance measurements.

There is illustrated in FIG. 1 a preferred embodiment of the particle analyzing apparatus, generally identified by the numeral 10. In this embodiment, the apparatus 10 comprises a reflector 12 having a concave reflector surface 14. This particular concave reflector surface 14 has the configuration of a portion of an ellipsoid (ellipse rotated about its major axis). The concave reflector surface 14 has a first focus 16 and a second focus 18 disposed along an optical axis 20. The forward opening of the reflector 12 preferably is closed off by a spherical transparent closure 22, having its center of curvature at the second focus 18. The reflector 12 and the closure 22 define a liquid-filled reflector chamber 24 for containing an electrically conductive liquid, such as a saline solution. The above-described reflector arrangement is of conventional design and can take many different configurations, as will be explained in detail hereinafter.

The first focus 16 is irradiated by a source 26 of illumination or radiant energy, to define a detection volume or optical sensing zone 27 in the reflector 12 at the first focus 16. Illumination of the optical sensing zone 27 can be accomplished in several conventional ways. One illumination technique is illustrated in FIG. 1, wherein the source 26 provides a substantially collimated laser beam which is initially centered on an optical axis 28. The laser beam reflects from a mirror 30 and proceeds along the optical axis 20 to irradiate the first focus 16. A transparent light port 32 is centered on the optical axis 20 to allow the laser beam to exit from the reflector 12 into a radiation beam dump 34.

The apparatus 10 has an entraining structure 36 for entraining a stream of individually isolated particles. The particle entraining structure 36 has a sample introduction tube 38; a sheath tube 40 positioned in surrounding, concentric relationship to the introduction tube 38; an exit tube 41 coaxially aligned in spaced apart relationship to the tubes 38 and 41; and a microscopic orifice 42, for example having a diameter of 100 micrometers, positioned at the end of the exit tube 41. A liquid stream of suspended particles, originating from a particle source 44 in the form of a pressurized reservoir, proceeds through the introduction tube 38. A laminar liquid sheath, originating from another pressurized reservoir 46 for sheath flow liquid, proceeds through the sheath tube 40 to surround the stream of particles so as to reduce the diameter of the stream of particles. The continuously decreasing inner diameter of the sheath tube 40 causes the liquid sheath to reduce the diameter of the liquid stream of particles after they exit from the introduction tube 38. Additionally, the relative velocities and flow rates of the liquid stream of suspended particles and the liquid sheath are determined by a conventional differential pressure regulator system. As the pressure and velocity of the liquid sheath is increased with respect to those of the liquid stream of particles, the diameter of the liqulid stream of particles is reduced. The liquid sheath also acts to center the stream of particles so that particles pass into the reflector chamber 24 along a trajectory 48 which intersects and passes through the first focus 16. The use of the sheath tube 40 and the liquid sheath is preferred, but not necessary. If they are eliminated, a wider illuminating beam must be used to obtain the same level of optical signal resolution. The reflector chamber 24 contains a second sheath liquid provided in a conventional manner by one or more inlet tubes 50 from a pressurized reservoir 51. The liquid for the second sheath is introduced through at least one of a pair of inlet tubes 50, with the presence of the two inlet tubes 50 allowing for the flushing of the chamber 24. It is desirable to have a second liquid sheath to provide sufficient hydrodynamic pressures to maintain the alignment of the particles with the trajectory 48 and to pass the particles through the chamber 24 into the exit tube 41. The particles proceed through the exit tube 41 and a tube 51 into a downstream chamber 52, with the liquid overflow going into a suitable waste reservoir 54.

The downstream vessel 52 contains an electrode 53 formed of an electrically conductive material and serves in the preferred embodiment as a downstream electrode for the orifice 42. The reflector 14 likewise is formed of an electrically conductive material and serves as an upstream electrode for the orifice 42. The introduction tube 38, the sheath tube 40 and the exit tube 41 are composed of suitable electrically non-conducting materials.

As can be seen from the enlarged fragmentary view of FIG. 2, the orifice 42 is formed in a wafer 56, such as of Sapphire positioned at the end of the exit tube 41. In a known manner, a D.C. electric current and/or a high frequency current is provided by an energizing source 58, which is electrically coupled respectively to the reflector surface 14 and the electrode 53 by electrical conductors 60 and 62. Since the orifice 42 provides the only fluid connection between the reflector chamber 24 and the interior of the exit tube 41, an electric field is established in and around the orifice 42, defining an impedance sensing zone 64, which is downstream from the optical sensing zone 27, but could likewise be upstream, as will be described hereinafter. The electrical circuit through the orifice 42 is coupled in a conventional manner to an impedance detector 66 for sensing impedance changes as the particles pass through the orifice 42. If energized by a current having a frequency in the radio spectrum or higher, the resultant signal is due not only to size, but to the combined effects of size, shape, resistivity and reactance. Circuitry for energizing the orifice 42 and detecting impedance changes is disclosed in U.S. Pat. Nos. 3,502,973 and 3,502,974 to Coulter et al.

After the particles exit from the sheath tube 40, they proceed along the trajectory 48 so as to traverse the laser beam in the optical sensing zone 27. Scattered radiation and/or stimulated fluorescent radiation proceeds from the first focus 16, reflects off the elliptical concave reflector surface 14, passes through the transparent closure 22 so as to converge on the second focus 18 and be collected by a conventional optical detector 68. The optical detector 68 typically comprises a photomultiplier cell with its associated optical elements. The collection of the radiation is shown for example by light ray 70. The collection and detection of the resultant optical signals is known in the art, as shown in the incorporated references. Also, if desired, absorbance measurements can be made, for example, by detecting and quantifying the radiation passing through the port 32.

The reflector 12, in the configuration of approximately one half of an ellipsoid as shown in FIG. 1, is merely illustrative of one of many different reflectors that can be used to collect a large percentage of the radiation proceeding from the first focus 16. There are several other reflector arrangements that are suitable for use in the present invention in that each has a reflector surface or surfaces that subtend a large solid angle with respect to the first focus 16. Examples of other suitable reflector arrangements are shown in previously cited and incorporated U.S. Pat. Nos. 4,188,542, 4,188,543, 4,189,236, and 4,199,686. Thereby, it can be seen that the reflector 14 can comprise any substantially conic section of revolution which is rotated about the optical axis 20. Hence, the reflector 12 can have a ellipsoidal, paraboloidal or hyperboloidal configuration and there can be additional reflector surfaces used in combination with the reflector 12. Moreover, the collected radiation can be reflected more than once. However, in each case, the reflector 12 has a focus whereat the optical signals originate, and these signals are reflected from the reflector 12 so as to be focused on a second focus, which can be at infinity or can be a virtual focus. It should be understood that, depending upon the reflector arrangement, portions of the radiation may not be reflected from the reflector 12, yet may still be collected, for example directly, for the purpose of collecting data therefrom. Moreover, some deviation from a strictly conic section configuration for the reflector 12 can be compensated for in most of reflector arrangements.

The chamber 24 defines a first vessel containing a first electrode, which is in the form of the concave reflector surface 14 and is disposed in an electrolyte solution. The interior of the exit tube 41 and the downstream vessel 52 define a second vessel containing a second electrode, which is in the form of the reflector surface 14 and is disposed in an electrolyte solution. The orifice 42 establishes a constricted path between the electrodes by providing a passageway between the two vessels for a sample flow of the electrolyte solution having the particles suspended therein.

For each particle analyzed, the impedance measurement and optical measurement are correlated, using conventional electrical circuitry, such as illustrated in the previously mentioned U.S. Pat. No. 3,710,933. As is known, correlation of signals on a particle-by-particle basis provides for more extensive particle analysis.

The diameter of the end of the tip 72 of the sheath tube 40 can be, for example, 500 micrometers, with the inner diameter being, for example, 70 micrometers. On the other hand, due to the requirements for physical strength, the end of the tip 74 of the exit tube 41 will have a diameter of at least 1000 micrometers and preferably more. Hence, the sheath tube 40 can be positioned substantially closer to the optical sensing zone 27 than the exit tube 41, and will still subtend approximately the same solid angle with respect to the first focus 16. For instance, as shown in FIGS. 1 and 2, the tip 72 of the sheath tube 40, with a 500 micrometers diameter, can be positioned so as to be 1000 micrometers from the first focus 16, while the tip 74 of the exit tube 41, with a 2000 micrometers diameter, can be positioned so as to be 4000 micrometers from the first focus 16. The tip 72 of the sheath tube 40 progressively increased in diameter with respect to displacement from the first focus 16, so as to maximize the usage of the spacial region of lost light collection, caused by the tip 72. Consequently, the increasing diameter allows for the upstream placement of the sample introduction tube 38 in the confines of the sheath tube 40. Moreover, by being able to position the sheath tube 40 close to the first focus 16, excellent alignment of the optical sensing zone 27 with the stream of particles can be achieved. This is a significant advantage resulting from the orifice 42 being positioned downstream of the optical sensing zone 27. More specifically, the exact coaxial alignment of the sheath tube 40 and the exit tube 41 in practice has proven to be a difficult adjustment subject to inaccuracies. However, even if the exit tube 41 and the orifice 42 mounted therein are slightly misaligned with respect to the sheath tube 40, the second sheath will hydrodynamically focus the stream of particles sufficiently to achieve the desired centering for the orifice 42. Also, such misalignment will not significantly effect the centering of the particles through the optical sensing zone 27. Moreover, the downstream positioning of the orifice 42, and therefore the impedance sensing zone 64, allows for the laminar, non-turbulant development of the concentric particle suspension and liquid sheath prior to reaching the closely positioned optical sensing zone 27. In otherwords, this design allows the sheath tube 40 to have a continuous, non-interrupted interior, since the wafer or orifice disc 56 need not be mounted therein. Additional advantages of this arrangement are that, due primarily to the first sheath, the particles are hydrodynamically centered through the optical sensing zone 27, while at the same time the remote positioning of the optical sensing zone 27 with respect to the exit tube 41 and orifice 42 maximizes the collection of detectable signals by minimizing the total solid angle of lost light collection created by the sheath tube 40 and the exit tube 41. Moreover, collection of detectable signals reflecting from the reflector 12 is increased by decreasing the extention of the exit tube 41 into the chamber 24. In a few applications it may be desirable to depart from this normally very advantageous remote positioning of the optical sensing zone 27 and assume greater losses in light collection. For instance, where the rate of particles being processed is very high, coincidence problems greatly increase, and it can be desirable to have the optical sensing zone 27 and the impedance sensing zone 64 closely spaced.

As previously mentioned, in some applications, the embodiment of FIGS. 1 and 2 can be implemented with a single sheath. In such a case, the only tube used to introduce the sample suspension of particles would be the tube 40. Also, there would only be one sheath, the sheath formed in the chamber 24, instead of the two sheaths shown in the drawings. The introduction tube 38 would be eliminated, making the tube 40 no longer a tube for providing a sheath, but a tube only for introducing the sample suspension into the reflector chamber 24. In this modified design, a wider illuminating beam would be required to provide the same degree of optical signal resolution that was achieved with the concentric tubes 38 and 40. Hence, substantially greater cost is required for the laser implementation of the illuminating beam. Alternatively, poorer optical resolution would have to be accepted. On the other hand, the liquid sheath provided in the reflector chamber 24 will hydrodynamically focus the particles through the sensing orifice 42. Again, the remote positioning of the optical sensing zone from the orifice 42 is very advantageous for light collection, unless particle coincidence and like problems require closely spaced optical and sensing zones 27 and 64. For the purpose of definition, the sheath 40 and the sample introduction tube 38 will both be referred to in the appended claims as "entrance tubes". In those embodiments wherein there is a single liquid sheath, there is only one entrance tube. In those embodiments wherein there are two liquid sheaths, there are two concentric entrance tubes.

If sorting of liquid droplets containing particles is desired, in a well known manner described in the previously mentioned U.S. Pat. No. 3,710,933, then an alternative embodiment, as shown in FIGS. 3 and 4, can be a preferred design. In the embodiment of FIGS. 1 and 2, a novel arrangement of the entraining means 36 allows for the orifice 42 to be positioned downstream of the optical sensing zone 27. This arrangement allows for good particle alignment with the optical sensing zone 27, while minimizing the lost light collection. In the hereinafter described embodiment of FIGS. 3 and 4, the orifice 42 is mounted upstream of the optical sensing zone 27. This arrangement can be desirable where formation of charged droplets, containing the particles, from the stream exiting from the exit tube 41 and sorting of the charged droplets are desired. More specifically, the pressure drop of the exit tube 41 can be minimized, the hydrodynamic focusing of the particles can be substantially maintained while they pass through the exit tube 41, and the downstream electrode, preferably in the form of the reflector 12, is conveniently located. Even where sorting is not desired, this embodiment provides a reasonable design alternative to that shown in FIGS. 1 and 2. On the other hand, where sorting is desired in the embodiment of FIGS. 1 and 2, the downstream electrode under the orifice 42 can take the form of preferably a frit and/or gel, as shown in U.S. Patent Application Ser. No. 967,773 to Leif, or a less desirable ring electrode, as shown in U.S. Pat. No. 3,380,584 to Fulwyler. Also, the exit tube 41 should be retracted from the chamber 24 and reduced in length to the greatest degree possible without losing the upstream hydrodynamic focusing, so as to minimize the downstream region in the exit tube 41 wherein there is weak hydrodynamic focusing. Where the upstream hydrodynamic focusing permits, the positioning of the orifice 42 can approach a virtually flush relationship with the reflector surface 14, thereby allowing, for example, another sheath to be introduced downstream of the orifice 42 to provide hydrodynamic focusing and to provide an electrical path to a downstream electrode.

FIG. 3 illustrates an alternative embodiment of the apparatus 10. Similar elements to those in FIGS. 1 and 2 will be identified by the same reference numerals. The particle entraining structure 36 has the sample introduction tube 38; the sheath tube 40 positioned in surrounding, concentric relationship to the introduction tube 38; and the microscopic orifice 42 positioned at the end of the sheath tube 40. A liquid stream of suspended particles, originating from the particle source 44 proceeds through the introduction tube 38. A laminar liquid sheath, originating from the pressurized reservoir 46 for sheath flow liquid, proceeds through the sheath tube 40 to surround the stream of particles so as to reduce the diameter of the stream. The liquid sheath also acts to center the stream of particles so that particles pass through the orifice 42 along the trajectory 48 which intersects and passes through the first focus 16. After leaving the orifice 42, the particles enter the liquid filled chamber 24. The reflector chamber 24 contains a second sheath liquid provided in a conventional manner by one or more of the inlet tubes 50. Due to the pressure drop associated with the orifice 42, it is particularly desirable to have a second liquid sheath to provide sufficient hydrodynamic pressures to keep the particles aligned with the trajectory 48 and to pass the particles through the chamber 24 into the exit tube 41. The particles proceed through the exit tube 41 to a suitable waste reservoir 54 positioned outside of the reflector 12.

The sample introduction tube 38 is, for example, composed of an electrically conductive material and serves in the alternative embodiment as an upstream electrode for the orifice 42. Alternatively, the upstream electrode could take the form of an electrode remotely positioned in an upstream chamber which is in fluid and electrical communication with the liquid sheath. The reflector 14 likewise, for example, is formed of an electrically conductive material and serves as a downstream electrode for the orifice 42. The sheath tube 40 and exit tube 41 are composed of a suitable non-conducting material.

As can be seen from the enlarged fragmentary view of FIG. 4, the orifice 42 is formed in the wafer 56, which is positioned at the end of the sheath tube 40. In a known manner, a D.C. electric current and/or a high frequency current is provided by the energizing source 58, which is electrically coupled respectively to the introduction tube 38 and the reflector surface 14 by the electrical conductors 60 and 62. Since the orifice 42 provides the only fluid connection between the sheath tube 40 and the chamber 24, an electric field is established in and around the orifice 42, defining the impedance sensing zone 64, which is upstream from the optical sensing zone 27, contrary to the preferred embodiment. After the particles pass through the impedance sensing zone 64, they proceed along the trajectory 48 so as to traverse the laser beam in the optical sensing zone 27. In all other respects, this alternative embodiment operates in a similar manner to the preferred embodiment of FIGS. 1 and 2.

With respect to FIGS. 3 and 4, although the use of the introduction tube 38 is desirable in most applications for hydrodynamically focusing the particles, the entraining structure 36 can be used without the introduction tube 38. In such a case, the reservoir 46 would contain a diluted suspension of the particles and there would be only one liquid sheath; the liquid sheath provided by the reflector chamber 24. In this variation to the embodiment of FIGS. 3 and 4, the stream of particles would not be hydrodynamically focused as they pass through the orifice 42. The diameter of the liquid stream of particles in the reflector chamber 24 is progressively reduced as it proceeds toward the exit nozzle 41. Hence, it is desirable to remotely position the optical sensing zone 27 with respect to the orifice 42 for two reasons. First, the stream will be more hydrodynamically focused toward the exit tube 41. Secondly, since the tip 74 of the exit nozzle 41 can be made relatively small with respect to the tip of the orifice containing tube 40, it is desirable to position the optical sensing zone 27 substantially closer to the exit nozzle 41 than to the tube 40, in order to minimize the solid angle of lost light collection of detectable signals.

With respect to FIGS. 3 and 4, the optical sensing zone is positioned adjacent the exit tube 41 for the above described reason of maximizing the collection of detectable signals. However, as described with respect to the preferred embodiment, coincidence problems and like problems in some applications can possibly make it desirable to have the optical sensing zone 27 and the impedance sensing zone 64 closely spaced. In such a case, less detectable signal collection would be possible, but, when the sample introduction tube 38 is used, the particles would remain hydrodynamically focused throughout the entire distance between the sheath tube 40 and the exit tube 41. Consequently, the particles would be hydrodynamically focused or centered in the optical sensing zone 27, no matter where the zone 27 is positioned along trajectory 48. On the other hand, the positioning of the optical sensing zone 27 in close proximity to the exit tube 41, as shown in FIGS. 3 and 4, has the disadvantage of the previously discussed alignment problems of the tubes 40 and 41, but has the advantage of being focused by two consecutive liquid sheaths.

With respect to FIGS. 3 and 4, the sheath tube 40 defines a first vessel containing a first electrode, which is, for example, in the form of the introduction tube 38 and is disposed in an electrolyte solution. Those skilled in the art will recognize that only a portion of the chamber 24 can be used in some variations of the apparatus 10 for the second vessel, if desired. The orifice 42 establishes a passageway between the two vessels for a sample flow of the electrolyte solution having the particles suspended therein.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzing apparatus for detecting the physical properties of particles, said particle analyzing apparatus including first vessel means containing a first electrode disposed in a first quantity of electrolyte, second vessel means containing a second electrode disposed in a second quantity of electrolyte, orifice means for establishing a constricted electrical path between said electrodes by providing a passageway between the vessel means for a sample flow of one of said quantities of electrolyte having a stream of said particles suspended therein, means for energizing said electrodes to provide an electrical current through said orifice means, means for detecting the impedance of said constricted electrical path, the particle analyzing apparatus further comprising:

said second vessel means being defined by at least a portion of a reflector chamber;

said reflector chamber including a concave reflector surface with a first focus and a second focus;

means for moving said stream of particles through said first focus;

a source of radiant energy arranged to irradiate the particles as they pass through said first focus to produce a source of detectable radiation signals at said first focus; and means for detecting the detectable radiation signals after they have been reflected from said concave reflector surface.

2. The particle analyzing apparatus according to claim 1, wherein said means for moving said stream of particles through said first focus includes an entrance tube for introducing said stream of particles into said reflector chamber and an exit tube, coaxially aligned with said entrance tube, for removing said stream of particles after they have passed through said first focus, said orifice means is positioned at the end of one of said tubes.

3. The particle analyzing apparatus according to claim 2, wherein said first focus is disposed in a close proximity relationship with respect to said tube not having said orifice means positioned therein and is remotely disposed with respect to said tube having said orifice means positioned therein, whereby the total solid angle subtended by said tubes, with respect to said first focus, is minimized so as to maximize the collection of said detectable radiation signals.

4. The particle analyzing apparatus according to claim 2, wherein said first focus is positioned closer to said tube not having said orifice means positioned therein than said tube having said orifice means positioned therein, whereby the total solid angle subtended by said tubes, with respect to said first focus, is minimized so as to maximize the collection of said detectable radiation signals.

5. The particle analyzing apparatus according to any one of claims 2, 3 or 4, wherein said orifice means is mounted in said exit tube.

6. The particle analyzing apparatus according to claim 5, further including,
   means for providing a liquid sheath around said stream of particles while the particles are in said entrance tube,
   said means for providing a liquid sheath including a second entrance tube coaxially positioned inside of said first recited entrance tube.

7. The particle analyzing apparatus according to claim 6, wherein said means for moving said stream of particles through said first focus includes means for providing a liquid sheath around said stream of particles after they exit from said first recited entrance tube.

8. The particle analyzing apparatus according to claim 7, wherein said means for providing a liquid sheath after the particles exit from said first recited entrance tube includes means for providing liquid to said reflector chamber.

9. The particle analyzing apparatus according to claim 1, wherein at least a portion of said first vessel means comprises an exit tube, said exit tube having said orifice means positioned at the end thereof, said exit tube being oriented toward said first focus in spaced apart relationship therewith to receive said stream of particles after they have passed through said first focus.

10. The particle analyzing apparatus according to claim 9, wherein said means for moving said stream of particles through said first focus comprises an entrance tube arranged and oriented to inject the stream of particles into said reflector chamber and toward said first focus, said entrance tube being coaxially disposed with said exit tube and oriented to face toward said first focus and said exit tube.

11. The particle analyzing apparatus according to claim 10, wherein said entrance tube includes a tapered tip having an end, said exit tube having an end containing said orifice means, said end of said entrance tube having a smaller outer periphery than the periphery of said end of said exit tube, said end of said entrance tube being spaced apart from said first focus by a smaller distance than the end of said exit tube is spaced from said first focus.

12. The particle analyzing apparatus according to claim 11, wherein said means for moving said stream of particles through said first focus includes means for providing a liquid sheath around said stream of particles after they exit from said first entrance tube.

13. The particle analyzing apparatus according to any one of claims 10, 11 or 12, further including,
   means for providing a liquid sheath around said stream of particles prior to the particles exiting from entrance tube.

14. The particle analyzing apparatus according to claim 1, wherein said second electrode comprising said concave reflector surface formed of a conductive material.

15. The particle analyzing apparatus according to any one of claims 2, 3 or 4, wherein said orifice means is mounted in said entrance tube.

16. The particle analyzing apparatus according to claim 15, further including,
   means for providing a liquid sheath around said stream of particles while the particles are in said entrance tube.

* * * * *